United States Patent [19]

Daren

[11] Patent Number: 4,967,026
[45] Date of Patent: Oct. 30, 1990

[54] PROCESS FOR THE PRODUCTION OF CHLOROMETHYL PHENETHYL BROMIDE

[75] Inventor: Stephen Daren, Ness Ziona, Israel

[73] Assignee: Bromine Compounds Ltd., Beer-Sheva, Israel

[21] Appl. No.: 350,399

[22] Filed: May 11, 1989

[30] Foreign Application Priority Data

May 12, 1988 [IL] Israel .......................................... 86366

[51] Int. Cl.$^5$ ....................... C07C 17/32; C07C 25/28
[52] U.S. Cl. ................................... 570/194; 570/196; 570/197; 570/198; 570/205
[58] Field of Search ............... 570/194, 196, 197, 198, 570/204

[56] References Cited

U.S. PATENT DOCUMENTS 1,910,462  5/1931  Brunner et al. ...................... 570/194
2,219,873  10/1940  Pinkernelle .......................... 570/194
3,069,480  12/1962  Hirth et al.
4,045,501  8/1977  Bianchi.

FOREIGN PATENT DOCUMENTS 10327  6/1964  Japan ................................... 570/194
3774   2/1965  Japan ................................... 570/194

Primary Examiner—Werren B. Lone
Attorney, Agent, or Firm—Michael N. Meller

[57] ABSTRACT

A process is described for preparing chloromethyl phenethyl bromide, in which phenethyl bromide is reacted with HCl and formaldehyde in the presence of zinc chloride as the catalyst, and in a chlorinated hydrocarbon as the solvent. The product is produced in yields in excess of 70%, the para isomer constituting more than 75% of the product which contains a mixture of ortho, meta and para isomers.

16 Claims, No Drawings

PROCESS FOR THE PRODUCTION OF CHLOROMETHYL PHENETHYL BROMIDE

The present invention relates to an improved process for the production of chloromethyl phenethyl bromide and to a new improved method for the production of chloromethyl styrene, utilizing said process as a first step for said chloromethyl styrene production.

Although scarcely used before 1972 chloromethyl styrenes have been the subject of an increasing number of publications and patents since then. According to Camps et al., J. of Macromolecular Science-Chemistry and Physics. Reviews in Macromolecular Chemistry C22(3) 343–407 (1982), the yearly average is now about 40 publications.

These monomers are useful intermediates in the preparation of other monomers by nucleophylic substitution, according to the reaction

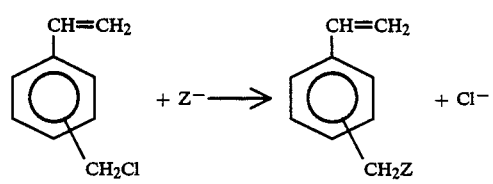

The Z groups, which may be of varied polarities, do not have a great effect upon the double bond owing to the saturated carbon intercalated between Z and the benzene ring, which explains the easy radical polymerization of these monomers. Thus it is relatively easy to synthesize functionalized polymers according to different industrial specifications, e.g. ion exchange resins, surfactants, dyes, grafted copolymers, elastomers, etc.

Chloromethyl styrenes are commercially available in the U.S.A. and Japan but at prices which are prohibitive for many applications. A need exists for a process which would produce high grade chloromethyl styrenes at more attractive prices.

A possible route for such a synthesis would utilize phenethyl bromide as a starting material using the following sequence of reactions:

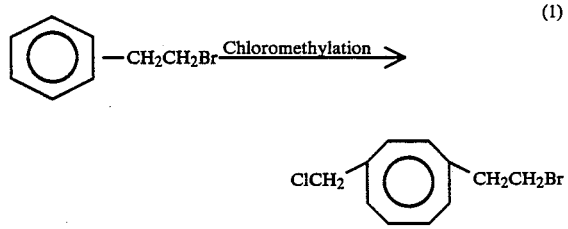

While this reaction sequence is to be found in the chemical literature the reported methods leave much to be desired if it is to form the basis of a viable process. This patent relates to improvements to both reactions (1) and (2).

Kondo et al (Shuji Kondo et al. J. Macromol. Sci. Chem A13(6), pp. 767–775 (1979)) chloromethylated phenethyl bromide using paraformaldehyde and hydrogen chloride. However he used the highly obnoxious and carcinogenic carbon disulfide as solvent as did Janovic. (Janovic, Z., Saric, K., Croat Chem. Acta 48(1), 59 (1976). Other authors (Janovic, Z., Saric, K., Croat Chem. Acta 48(1), 59 (1976); Shinka et al. J. Poly. Sci. Polym. Lett. Ed., 14(1), 1, (1976); Shigeo T. Synth. Commun 4(4), 193–197 (1974); Shigeo T. et. al. Chem. Abst. 72:32290 (1970)), have chloromethylated phenethyl bromide using the free chloromethyl ether which is equally undesirable since it too is an extremely dangerous carcinogen. As catalysts both aluminum chloride (Shinka et al. J. Poly. Sci. Polym. Lett. Ed., 14(1), 1, (1976); Shigeo T. Synth. Commun 4(4), 193–197 (1974); Shigeo T. et. al. Chem. Abst. 72:32290 (1970)) and stannic chloride (Janovic, Z., Saric, K., Croat Chem. Acta 48(1), 59 (1976)) gave poor yields.

Gozdz (Gozdz A. S. Polymer Bulletin 4, 577–582 (1982)) bromomethylated phenethyl bromide by the in-situ generation of hydrogen bromide from excess sodium bromide mixed with glacial acetic acid and conc. sulfuric acid. After 8 hours at 85° C. about 46% phenethyl bromide was recovered and after recrystallization 16.8% of the desired para isomer was obtained.

According to the present invention there is now provided a process for the production of chloromethyl phenethyl bromide, comprising reacting phenethyl bromide with HCl and formaldehyde in the presence of zinc chloride as catalyst and a chlorinated hydrocarbon as solvent.

Said chlorinated hydrocarbon is selected from methylene chloride carbon tetrachloride, dichloroethane, trichloroethane, tetrachloroethane, orthodichlorobenzene, etc.

As opposed to the processes reported in the literature, according to the present process chloromethyl phenethyl bromide is produced in yields in excess of 70% which represents a significant and surprising improvement over the yields previously reported as shown in Table 1 hereinafter.

TABLE 1

Comparison of Various Chloromethylations of Phenethyl Bromide (Reaction 1).

| Solvent | Catalyst | Source of-CH$_2$Cl | Disadvantage | Yield | Author |
|---|---|---|---|---|---|
| Carbon Disulfide | Zinc Chloride | HCl, paraformaldehyde | CS$_2$, carcinogen, smelly | 51% | Kondo et al |
| Carbon Disulfide | Stannic Chloride | Chloromethyl Ether (CME) | smelly, CME and CS$_2$ carcinogens | 44% Para | Janovic et al |
| Tetrachloroethane | Aluminum Chloride | Chloromethyl Ether (CME) | CME carcinogen | 31% | Shinka et al |

TABLE 1-continued

Comparison of Various Chloromethylations of Phenethyl Bromide (Reaction 1).

| Solvent | Catalyst | Source of -CH$_2$Cl | Disadvantage | Yield | Author |
|---|---|---|---|---|---|
| Tetrachloroethane | Aluminum Chloride | Chloromethyl Ether (CME) | CME carcinogen | 29% | Shigeo et al |
| Dichloroethane | Zinc Chloride | HCl, paraformaldehyde | no carcinogens, no smells, high yields. | >70% | Process of the present invention. |

Thus it can be seen that as opposed to the known prior art processes in which yields of only 29, 31, 44 and 51% were reported the process of the present invention provides yields in excess of 70% and in fact yields of about 80% were obtained.

Furthermore it has been found that when the chloromethylation process is carried out according to the present invention that said chloromethyl phenethyl bromide product is a mixture of ortho, meta and para isomers, the major component of said mixture being the para isomer which is viewed by chemists as the preferable isomer. In fact it has been found that said para isomer constitutes more than 75% of said mixture.

In a preferred embodiment of the present invention there is provided a two step process for producing chloromethyl styrene wherein chloromethyl phenethyl bromide is produced as defined above by reacting phenethyl bromide with HCl and formaldehyde in the presence of zinc chloride as catalyst and a chlorinated hydrocarbon as solvent followed by dehydrobromination to produce said chloromethyl styrene. Said dehydrobromination step can be by methods known per se or preferably by reacting said chloromethyl phenethyl bromide in a non-aqueous, single-phase alcoholic solution with an alkali hydroxide in the presence of a phase transfer catalyst and an alkali nitrite as co-catalyst to produce chloromethyl styrene.

In said second step said alkali hydroxide is preferably potassium hydroxide and said alcoholic solution comprises t-butanol.

A wide variety of phase transfer catalysts can be used in said step including crown ethers such as crown 16, crown 18; pseudo crown ethers such as polyethylene glycols and solid polymer supported phase transfer catalysts: chloromethylated polystyrene quaternized with trimethyl, triethyl (trialkyl) amines, etc.

Especially preferred for use are example quaternary ammonium salts of long and short amines or quaternary phosphonium salts which may be represented by the formula:

wherein R$_1$, R$_2$, R$_3$ and R$_4$ may be the same or different and is hydrogen alkyl, aryl, aralkyl, hydroxyalkyl or an alkoxyalkyl group and X is a nucleophilic anion.

Preferred anions of these catalysts include Cl$^-$, Br$^-$, CN$^-$, S$_2^-$, HS$^-$, NO$_3^-$, NO$_2^-$, ClO$_4^-$, ClO$_3^-$, RSO$_3^-$ and RCCO$^-$ wherein R is a known per organic group for such anions, e.g. toluene, naphthalene, acetate, salicylate etc.

Most preferred for use as phase transfer catalyst are quaternary ammonium salts such as tetrabutylammonium bromide, tetrabutylammonium hydrogen sulfate, triethylbutyl ammonium bromide, triethyl benzyl ammonium, chloride, trimethyl dodecyl ammonium chloride etc.

As co-catalyst there can be used potassium nitrite or sodium nitrite, however, sodium nitrite is preferred as the use thereof resulted in 96% conversion of chloromethyl phenethyl bromide and 80% yield of chloromethyl styrene in only 75 minutes at 35° C.

In the simplest form of the proposed process zinc chloride is the preferred catalyst and 1.2 dichloroethane is the preferred solvent. The chloromethylation is achieved using paraformaldehyde and hydrogen chloride gas supplied from a cylinder. Thus high yields and conversions are achieved while avoiding the use of such carcinogens as free chloromethyl ether and carbon disulfide.

As a further improvement the hydrogen chloride gas is generated in situ using zinc chloride and conc. sulfuric acid. Here too, high yields and conversions are achieved while saving the complications involved in using cylinders of hydrogen chloride gas. This process is also shown to be applicable to bromomethylations.

Since sulfuric acid is known to be a highly reactive but unselective catalyst for Friedel Crafts and other reactions it is important, in contradiction to Gozdz (Gozdz A. S. Polymer Bulletin 4, 577–82 (1982)) to ensure that the sulfuric acid is always fully consumed in generating the hydrogen chloride or bromide so that its excess cannot cause undesirable side reactions. This enables high yields to be achieved while generating the hydrogen halide gas in situ. In his reaction Gozdz achieved only 54% conversion and only 16.8% yield of crystallized product.

For the dehydrobromination reaction (Shuji Kondo et al. J. Macromol. Sci. Chem A13(6), pp. 767–775 (1979)), and several other authors have utilized sodium or potassium alcoholates (Shuji Kondo et al. J. Macromol. Sci. Chem. A13(6) pp. 767–775 (1979); Shinka et al. J. Poly. Sci. Polym. Lett. Ed., 14(1), 1, (1976); Shigeo T. Synth. Comm. 4(4) 193–7 (1974); Shigeo T. et. al. Chem. Abst. 72:32290(1970)) and have achieved yields on this step of up to 87% (Shuji Kondo et al. J. Macromol. Sci. Chem A13(6), pp. 767–775 (1979)). However, the use of sodium or potassium metal is not convenient even on a laboratory scale and could hardly form the basis for a simple industrial process.

Other authors have used potassium hydroxide solutions in alcohols with poor yields (10.8%) (Janovic, Z., Saric, K., Croat Chem. Acta 48(1), 59 (1976). Tadatoni et al. (Tadatoni N. et al. Tetrahedren Lett., 22(39), 3873 (1981)) added a phase transfer catalyst to the KOH-t-butanol solution and achieved good yields (73%) but the reaction required 24 hours.

In the synthesis of bromostyrene from bromophenethyl bromide, Daren S. et al. U.S. Pat. No. 4,292,453, Sept. 29, 1981, greatly improved the kinetics of the phase transfer catalyzed dehydrobromination by the addition of catalytic quantities of sodium nitrite. However in those reactions Daren utilized aqueous bases which as will be shown in comparative example 5 hereinafter are unsuitable for the production of chloromethylstyrene since the chloromethyl group is readily hydrolyzed and mainly unwanted dimers are formed.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Showing the use of 1-2-Dichloroethane (DCE) Zinc Chloride and Paraformaldehyde with HCl gas from a cylinder.

Phenethyl bromide, 444 g (2.4 moles) and 1-2 dichloroethane (200 mls), were placed in a mechanically stirred 2 liter, 3 necked glass flask fitted with a sinter-glass inlet for hydrogen chloride gas. The outlet vent was protected with a cold trap ($-15°$ C.) and a calcium chloride drying tube. The flask was placed in a thermostated oil bath at $35°-40°$ C.

The hydrogen chloride cylinder was placed on a balance to record the loss in weight as the gas was released and was connected to the reaction vessel via a bubbler containing 1-2 dichloroethane as well as via two empty flasks acting as traps in the event of suckback due to a drop in pressure. The connecting tubes were either Teflon ® or Viton ®.

The zinc chloride 50 g (0.37 moles) which had previously been dried in an oven for 24 hours at $110°$ C. was mixed with the paraformaldehyde 60 g (2.4 moles). The mixture of solids was added to the reaction vessel in 3 portions during the course of the reaction by temporarily removing the cold-trap.

Hydrogen chloride gas 82 g (2.2 moles) was added during five hours. After five hours a gas chromatogram of the reaction mixture (ignoring the solvent) showed 61% unreacted phenethyl bromide
35% chloromethylated phenethyl bromide (o:m:p=2:1:12)
4% dimers.

Work Up

The lower clear phase was the water-soluble phase. The upper organic phase after separation was washed with water, dilute sodium carbonate and again with water. After drying over calcium chloride, the dichloroethane was distilled off from the product using a Rotovapor under-water vacuum. 520 g of crude product remained.

Fractional distillation of the crude product at 2.5 mm Hg (Tvap=75° C.) removed most of the unreacted phenethylbromide.

| Wt. Recovered phenethyl bromide | | = 218 g |
|---|---|---|
| Wt. Heavy Product | | = 265 g |
| Composition: | phenethyl bromide | = 12% |
| by G.C. | chloromethylphenethyl bromide | = 79% |
| | dimers | = 9% |

The heavy product solidified on standing overnight.

EXAMPLE 2

The procedure of Example 1 was repeated with the following modifications: The phenethylbromide and dichloroethane were presaturated with hydrogen chloride before adding the first portion of zinc chloride and formaldehyde.

Reaction continued for 23 hours.
Total HCl gas=87 g
Composition of reaction mixture by G.C. at end of reaction:
Unreacted phenethyl bromide=1%
Chloromethylated phenethyl bromide=87% (o:m:p=2:1:12)
dimers=8%
Wt. crude product after distillation of D.C.E.=537 g (2.3 moles nominally) (nominal yield=95%).

EXAMPLE 3

Showing the use of hydrogen chloride gas generated in situ

Phenethyl bromide, 37 g (0.2 moles) were placed in a 250 mls. three-necked flask fitted with a mechanical stirrer and cold-trap as in Example 1. Paraformaldehyde, 5.49 g (0.18 moles) was added while stirring. The mixture was maintained at $45°$ C. in an oil bath. Dried zinc chloride, 30 g (0.22 moles) was ground in a mortar and pestle under 1.2-dichloro ethane (20 mls) and the slurry was added to the flask.

Conc. $H_2SO_4$ (>98%) 14.7 g (0.15 moles) was added from a dropping funnel during one minute. The mixture initially turned red but the colour rapidly faded. The reaction was continued for 17 hours at $45°-50°$ C.

After washing the product and removing the dichloroethane 37 g (nominally 0.16 moles) of crude chloromethylated phenethyl bromide was obtained.

The composition of the crude materials by G.C. was:

| phenethyl chloride | = 1% |
|---|---|
| (due to halogen exchange) | |
| unreacted phenethyl bromide | = 14.5% |
| chloromethyl phenethyl chloride | = 2% |
| chloromethyl phenethyl bromide | = 68% (o:m:p = 2:1:5) |
| bromomethyl phenethyl bromide | = 2% |
| dimers | = 10% |

EXAMPLE 4

Showing the use of hydrogen bromide generated in situ for bromomethylation and the use of other bromides in addition to zinc bromide Since zinc bromide and zinc chloride are relatively expensive salts it is worthwhile using cheaper sources of hydrogen bromide such as calcium or sodium bromide. The addition of the inexpensive bromides plus sulfuric acid are carried out prior to the addition of the zinc bromide so that the catalyst is not consumed in the production of the hydrogen bromide.

Thus phenethyl bromide, 351.5 g (1.9 moles) 1.2-dichloroethane (100 mmls), sodium bromide, 103 g (1.0 moles), calcium bromide 16 g (0.08 moles) and paraformaldehyde 30 g (1.0 moles) were added to a mechanically stirred flask at 50° C. Conc. sulphuric acid (>98%). 103 g (1.05 moles) was drip-fed into the mixture during 5 minutes. Oven dried zinc bromide, 50 g (0.25 moles) was ground in a mortar under 50 mls 1.2.D.C.E. and then added to the reaction mixture. After two hours repeat quantities of paraformaldehyde, sodium and calcium bromide, sulfuric acid and zinc bromide were added to the reaction mixture in the same order as above and the reaction was continued for a total of 18 hours. At the end of this time most of the solids had dissolved and the phases could be easily separated.

The gas chromatogram of the organic layer had the following composition:

| | |
|---|---|
| unreacted phenethyl bromide | = 4% |
| bromomethylated phenethyl bromide | = 86% (o:m:p = 3:1:13) |
| dibromomethylated phenethyl bromide | = 8% |

The chromatogram in this case is much simpler than the chloromethylation (Example 3) since there is no halogen exchange between bromine and chlorine atoms.

The organic layer was washed twice with 100 mls. 10% hydrobromic acid to remove all the salts and finally washed with distilled water. After distillation of the dichloroethane (water vacuum at 50 C, followed by oil vacuum at 70 C) a black residue remained which solidified on standing overnight.

Wt. bromomethylated phenethyl bromide=502 g (1.8 moles nominally) (nominal yield 95%).

COMPARATIVE EXAMPLE 5

Dehydrobromination under phase transfer conditions as in U.S. Pat. No. 4,292,453

Chloromethylated phenethyl bromide (from example 1) 46 g (nominally 0.2 moles) containing 12% phenethyl bromide was rapidly mixed with 45% NaOH, 61 g (0.8 moles), triethylbutyl ammonium bromide (40% aqueous solution), 1.25 g and sodium nitrite (0.2 g) for 90 mins. at 70°-80° C. At the end of this time the gas chromatogram showed that all the phenethyl bromide had been converted to styrene but the chloromethylated phenethyl bromide had produced approximately 50% dimers (possibly ethers) while the remaining monomeric product was an equal mixture of chloromethyl styrene and methanol styrene.

From the above examples it can be seen that the use of aqueous sodium hydroxide under phase transfer conditions and in the presence of sodium nitrite produces 50% unwanted dimers and a monomer mixture only half of which is the desired chloromethylstyrene.

EXAMPLE 6

Dehydrobromination in an alcoholic medium

Chloromethyl phenethyl bromide containing 1% phenethyl bromide (from example 2) 97.7 g (0.42 moles), triethylbutyl ammonium bromide (40% aqueous solution) 3 g, and sodium nitrite (0.5 g) were mechanically stirred in a 3 necked 1l. flask maintained at 35° C. in a water bath.

Potassium hydroxide pellets, 73 g (1.3 moles) were dissolved in 488 mls. analytical t-butanol. The potassium hydroxide solution was added to the reaction flask during 5 minutes and the reaction was continued for a total of 75 mins.

After this time the gas chromatogram showed the following composition of crude monomer:

| | |
|---|---|
| styrene | = 0.5% |
| chloromethyl styrene | = 82% |
| bromomethyl styrene | = 1.5% |
| unreacted chloromethyl phenethyl bromide | = 4% |
| dimers | = 10% |

Work up

The reaction mixture was filtered to remove solids and then cooled in an ice-bath. A minium quantity of conc. hydrochloric acid was carefully added to neutralize the excess potassium hydroxide. A white emulsion which slowly separated out was obtained. Addition of a small amount of hexane improved the separation. The organic layer was distilled at 80° C. under water vacuum to remove the solvents. A crude liquid residue, 79 g, was obtained.

The residue was drip fed into a 50 mls. distillation flask fitted with a 10 cms. Vigraitte column. The hot liquids were magnetically stirred. The flask was maintained at 130° C. in a oil bath under a vacuum of 0.2 mmHg. These conditions caused a rapid flash distillation of the monomer which was collected in a receiving flask cooled on ice.

Chloromethyl styrene, 41.8 g, was obtained as a distillate and stabilized with 100 ppm tert. butyl catechol.(T.B.C.). Percentage yield on the 2 combined steps is 62% based on phenethyl bromide. Heavy residues were 12.9 g. The G.C. of the distillate showed the material to be >96% chloromethyl styrene and a combined peak integrated to approximately 4% bromomethyl styrene and unreacted chloromethylated phenethylbromide.

The chlorine content of the monomer was determined by combustion to be 21.3% (Theoretical=23.3%).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the production of chloromethyl phenethyl bromide, comprising reacting phenethyl bromide with HCl and formaldehyde in the presence of zinc chloride as catalyst and a chlorinated hydrocarbon as solvent.

2. A process according to claim 1 wherein said HCl is generated in situ from a non-Friedel Crafts catalyst halide salt and concentrated sulfuric acid.

3. A process according to claim 1 wherein said halide salt is selected from a group I or group II metal halide.

4. A process according to claim 1 wherein said halide salt is a chloride.

5. A process according to claim 1 wherein said chlorinated hydrocarbon is selected from methylene chloride, carbon tetrachloride, dichloroethane, trichloroethane, tetrachloroethane, orthodichlorobenzene.

6. A process according to claim 1 wherein said chlorinated hydrocarbon is dichloroethane.

7. A process for the production of chloromethyl phenethyl bromide according to claim 1 characterized in that said chloromethyl phenethyl bromide product is a mixture of ortho, meta and para isomers, the major component of said mixture being the para isomer.

8. A process according to claim 7 wherein said para isomer constitutes more than 75% of said mixture.

9. A process according to claim 7 wherein said chloromethyl phenethyl bromide is produced in yields in excess of 70%.

10. A process for the production of chloromethyl styrene according to claim 1, comprising reacting phenethyl bromide with HCl and formaldehyde in the presence of zinc chloride as catalyst and a chlorinated hydrocarbon as solvent followed by dehydrobromination to produce said chloromethyl styrene.

11. A process for the production of chloromethyl styrene according to claim 1 comprising reacting phenethyl bromide with HCl and formaldehyde in the presence of zinc chloride as catalyst and a chlorinated hydrocarbon as solvent to produce chloromethyl phenethyl bromide and then reacting said chloromethyl phenethyl bromide in a non-aqueous, single-phase alcoholic solution with an alkali hydroxide in the presence of a phase transfer catalyst and an alkali nitrite as co-catalyst.

12. A process according to claim 11 wherein said alkali hydroxide is potassium hydroxide.

13. A process according to claim 11 wherein said phase transfer catalyst is a quaternary ammonium salt.

14. A process according to claim 11 wherein said phase transfer catalyst is a triethyl butyl ammonium bromide.

15. A process according to claim 11 wherein said alkali nitrite is sodium nitrite.

16. A process according to claim 11 wherein said alcoholic solution comprises t-butanol.

* * * * *

UNITED STATES PATENT AND TRADEMARK OFFICE
CERTIFICATE OF CORRECTION

PATENT NO. : 4,967,026             Page 1 of 2
DATED     : October 30, 1990
INVENTOR(S) : DAREN It is certified that error appears in the above-identified patent and that said Letters Patent is hereby corrected as shown below:

Title page, left column, item [30], amend "86366" to read
--86365--

Column 1, after line 50, amend formula I to read

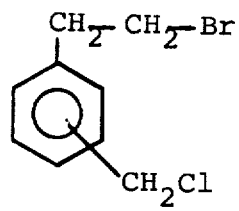

I

Column 2, line 5, amend formula II to read

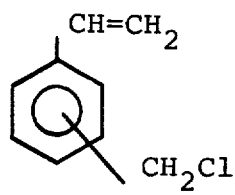

II

Column 5, line 2, insert --et al.-- after "Daren"

UNITED STATES PATENT AND TRADEMARK OFFICE
CERTIFICATE OF CORRECTION

PATENT NO. : 4,967,026

DATED : October 30, 1990

INVENTOR(S) : DAREN

It is certified that error appears in the above-identified patent and that said Letters Patent is hereby corrected as shown below:

Column 6, line 30, amend "wereplaced" to read --was placed-- line 65, amend "addition" to read --additions--

Signed and Sealed this

Ninth Day of February, 1993

Attest:

STEPHEN G. KUNIN

Attesting Officer

Acting Commissioner of Patents and Trademarks